US010639470B2

(12) United States Patent
Doi et al.

(10) Patent No.: US 10,639,470 B2
(45) Date of Patent: May 5, 2020

(54) LOW-FREQUENCY TREATMENT DEVICE, PAD FOR LOW-FREQUENCY TREATMENT DEVICE, MAIN BODY PORTION FOR LOW-FREQUENCY TREATMENT DEVICE, HOLDER FOR LOW-FREQUENCY TREATMENT DEVICE, AND COMBINATION OF PAD AND HOLDER FOR LOW-FREQUENCY TREATMENT DEVICE

(71) Applicant: OMRON HEALTHCARE CO., LTD., Muko-shi, Kyoto (JP)

(72) Inventors: Yoshiki Doi, Kyoto (JP); Shinji Nakazawa, Kyoto (JP); Kayoko Maeda, Kyoto (JP); Nobuhiko Osoegawa, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 184 days.

(21) Appl. No.: 15/901,324

(22) Filed: Feb. 21, 2018

(65) Prior Publication Data
US 2018/0177997 A1   Jun. 28, 2018

Related U.S. Application Data

(63) Continuation of application No. PCT/JP2016/075573, filed on Aug. 31, 2016.

(30) Foreign Application Priority Data

Sep. 4, 2015   (JP) ................ 2015-174545

(51) Int. Cl.
*A61N 1/04* (2006.01)
*A61N 1/32* (2006.01)
*A61N 1/36* (2006.01)

(52) U.S. Cl.
CPC ............. *A61N 1/0492* (2013.01); *A61N 1/04* (2013.01); *A61N 1/32* (2013.01); *A61N 1/36014* (2013.01)

(58) Field of Classification Search
CPC .... A61N 1/0452–0492; A61N 1/36014–36028
See application file for complete search history.

(56) References Cited

U.S. PATENT DOCUMENTS 4,033,356 A * 7/1977 Hara .................... A61N 1/0452
607/152
6,445,955 B1 * 9/2002 Michelson ......... A61N 1/36003
607/2

(Continued)

FOREIGN PATENT DOCUMENTS

JP   H06-001204 U   1/1994
JP   H06-339531 A   12/1994

(Continued)

OTHER PUBLICATIONS

Nov. 8, 2016 International Search Report issued in International Patent Application No. PCT/JP2016/075573.

(Continued)

*Primary Examiner* — Eric D. Bertram
(74) *Attorney, Agent, or Firm* — Oliff PLC

(57) ABSTRACT

The present invention includes a guiding engagement portion configured such that a holder and a main body portion for supplying a low-frequency pulse current to a pad engage in a state in which the main body portion is attached to the holder, and the holder and the main body portion are disengaged in a state in which the main body portion is removed. The guiding engagement portion is formed so as to allow the holder and the main body portion to engage by moving in a direction of approaching each other during the attachment, and during the removal, disengage the holder and the main body portion by restricting movement in a (Continued)

direction opposite to the movement direction during the attachment, and allowing the main body portion to move with respect to the holder in a direction intersecting the direction of approaching each other.

10 Claims, 7 Drawing Sheets

(56) References Cited

U.S. PATENT DOCUMENTS

| | | | | |
|---|---|---|---|---|
| 6,961,622 | B2* | 11/2005 | Gilbert | A61H 39/002 |
| | | | | 607/148 |
| 2015/0231393 | A1 | 8/2015 | Bachinski et al. | |
| 2017/0209693 | A1* | 7/2017 | An | A61N 1/0476 |
| 2018/0177998 | A1* | 6/2018 | Doi | A61N 1/04 |

FOREIGN PATENT DOCUMENTS

| | | |
|---|---|---|
| JP | H08-257141 A | 10/1996 |
| JP | 2002-179109 A | 6/2002 |
| JP | 2013-512076 A | 4/2013 |
| WO | 2015/199327 A1 | 12/2015 |

OTHER PUBLICATIONS

Sep. 6, 2019 Office Action issued in Japanese Patent Application No. 2015-174545.

* cited by examiner

LOW-FREQUENCY TREATMENT DEVICE, PAD FOR LOW-FREQUENCY TREATMENT DEVICE, MAIN BODY PORTION FOR LOW-FREQUENCY TREATMENT DEVICE, HOLDER FOR LOW-FREQUENCY TREATMENT DEVICE, AND COMBINATION OF PAD AND HOLDER FOR LOW-FREQUENCY TREATMENT DEVICE

REFERENCE TO RELATED APPLICATIONS

The present application claims priority based on Japanese Patent Application 2015-174545, which is incorporated in the description of the specification of the present application by reference.

TECHNICAL FIELD

The present invention relates to a low-frequency treatment device.

BACKGROUND ART

Conventionally, there has been a low-frequency device that performs a treatment such as relieving shoulder stiffness of a user due to a pad that includes a conductive layer being attached to the body of the user and a low-frequency pulse current being supplied to the body (see Patent Document 1).

With the low-frequency treatment device disclosed in Patent Document 1, a main body portion ("upper-half portion" in Patent Document 1) is attached to a holder ("lower-half portion" in Patent Document 1) with a pad ("electrode pad" in Patent Document 1) interposed therebetween. The holder and the main body portion are attached to each other by fitting protrusions on the holder into recessed portions formed on the main body portion. Attachment and removal of the two is performed by moving the main body portion in the vertical direction with respect to the holder.

Also, due to a terminal provided on the holder being electrically connected to the main body portion and the pad, current is applied from the main body portion to the pad via the holder.

However, in the attachment structure of the holder and the main body portion disclosed in Patent Document 1, the fitting is released if the user moves his or her body during use, or the like. Upon doing so, current is no longer applied to the pad, and therefore the treatment is interrupted. In this case, the user needs to re-attach the main body portion to the holder.

In this manner, the low-frequency treatment device according to Patent Document 1 has had room for improvement in that application of current to the pad becomes unstable in some cases.

CITATION LIST

Patent Literature

Patent Document 1: JP H6-339531A (FIGS. 3 and 4)

SUMMARY OF INVENTION

Technical Problem

In view of this, the present invention aims to provide a low-frequency treatment device, a pad for a low-frequency treatment device, a main body portion for a low-frequency treatment device, a holder for a low-frequency treatment device, and a combination of a pad and a holder for a low-frequency treatment device, according to which it is possible to stably apply current to a pad.

Solution to the Problem

The present invention is a low-frequency treatment device that includes: a pad that is to be attached to a body of a user and is configured to supply a low-frequency pulse current to the user; a holder configured to hold the pad; a main body portion configured to supply a low-frequency pulse current to the pad by being attached to the holder; and a guiding engagement portion configured such that the holder and the main body portion engage in a state in which the main body portion is attached to the holder, and the holder and the main body portion are disengaged in a state in which the main body portion is removed from the holder, wherein the guiding engagement portion is formed so as to allow the holder and the main body portion to engage by moving in a direction of approaching each other during the attachment, and during the removal, disengage the holder and the main body portion by restricting movement in a direction opposite to the movement direction during the attachment and allowing the main body portion to move with respect to the holder in a direction intersecting the direction of approaching each other.

Also, the guiding engagement portion can be formed such that during the removal, the holder and the main body portion are disengaged due to the main body portion being rotated with respect to the holder about an axis oriented in the direction of approaching each other.

Also, the guiding engagement portion can include a protrusion formed on one of the holder and the main body portion, and a groove portion formed on the other and in which the protrusion fits.

Also, the holder can include a set of wall portions that are located on both sides of the main body portion in the direction intersecting the direction of approaching each other, inner sides of the wall portions having a curved shape so as to allow rotation of the main body portion, on the inner surfaces of the wall portions, vertical groove portions that are formed in a vertical direction, which is the direction of approaching each other, and open upward, and a set of horizontal groove portions that are formed in the direction intersecting the vertical direction and are open at at least one end portion in a horizontal direction can be formed as the groove portions, and a set of main body portion-side protrusions that can move along the vertical groove portions and the horizontal groove portions can be formed on side surfaces of the main body portion that face the wall portions.

Also, at least one of the set of horizontal groove portions can be provided with a restricting portion that restricts rotation of the main body portion with respect to the holder in the direction intersecting the direction of approaching each other, from a state in which the main body portion is attached to the holder.

Also, the main body portion can include a main body portion-side electrode portion configured to supply a low-frequency pulse current to the pad, the main body portion-side electrode portion protruding from a surface facing the holder, the pad can include an attachment portion to be attached to the holder, the attachment portion can include a pad-side electrode portion on a surface facing the main body portion, and the main body portion-side electrode portion can come into contact with the pad-side electrode portion when the main body portion is attached to the holder, and thus a low-frequency pulse current can be supplied from the main body portion to the pad.

Also, the holder can be composed of a non-conductor.

Also, the present invention is a pad for a low-frequency treatment device, to be used in the low-frequency treatment device, the pad including: an attachment portion to be attached to the holder of the low-frequency treatment device, and a treatment portion that extends in at least one direction from the attachment portion and at which a conductive layer composed of a conductor is exposed, wherein a width dimension of the attachment portion is formed to be smaller than a width dimension of the treatment portion, and an outer circumferential edge of the attachment portion includes curve portions that approximately match the curves of the wall portions of the low-frequency treatment device.

Also, the present invention is a main body portion for a low-frequency treatment device that is configured to supply a low-frequency pulse current to a pad configured to be attached to a body of a user and supply the low-frequency pulse current to the user, by being attached to a holder for holding the pad, the main body including a guiding engagement portion configured such that the holder and the main body portion engage in a state in which the main body portion is attached to the holder, and the holder and the main body portion are disengaged in a state in which the main body portion is removed from the holder, wherein the guiding engagement portion is formed so as to allow the holder and the main body portion to engage by moving in a direction of approaching each other during the attachment, and during the removal, disengage the holder and the main body portion by restricting movement in a direction opposite to the movement direction during the attachment and allowing the main body portion to move with respect to the holder in a direction intersecting the direction of approaching each other.

Also, the present invention is a holder for a low-frequency treatment device configured to hold a pad that is to be attached to a body of a user and supply a low-frequency pulse current to the user, the holder being attached to a main body portion configured to supply the low-frequency pulse current to the pad, the holder including a guiding engagement portion configured such that the holder and the main body portion engage in a state in which the main body portion is attached, and the holder and the main body portion are disengaged in a state in which the main body portion is removed, wherein the guiding engagement portion is formed so as to allow the holder and the main body portion to engage by moving in a direction of approaching each other during the attachment, and during the removal, disengage the holder and the main body portion by restricting movement in a direction opposite to the movement direction during the attachment and allowing the main body portion to move with respect to the holder in a direction intersecting the direction of approaching each other.

Also, the present invention is a combination of a pad and a holder for a low-frequency treatment device, composed of a pad that is attached to the body of a user and supplies a low-frequency pulse current to the user, and a holder that holds the pad. In the combination of a pad and a holder for a low-frequency treatment device, the holder includes a guiding engagement portion configured such that the holder and a main body portion for supplying a low-frequency pulse current to the pad engage in a state in which the main body portion is attached, and the holder and the main body portion are disengaged in a state in which the main body portion is removed. The guiding engagement portion is formed so as to allow the holder and the main body portion to engage by moving in a direction of approaching each other during the attachment, and during the removal, disengage the holder and the main body portion by restricting movement in a direction opposite to the movement direction during the attachment, and allowing the main body portion to move with respect to the holder in a direction intersecting the direction of approaching each other.

Also, the holder can be composed of a non-conductor.

DESCRIPTION OF EMBODIMENTS

Figure 1:
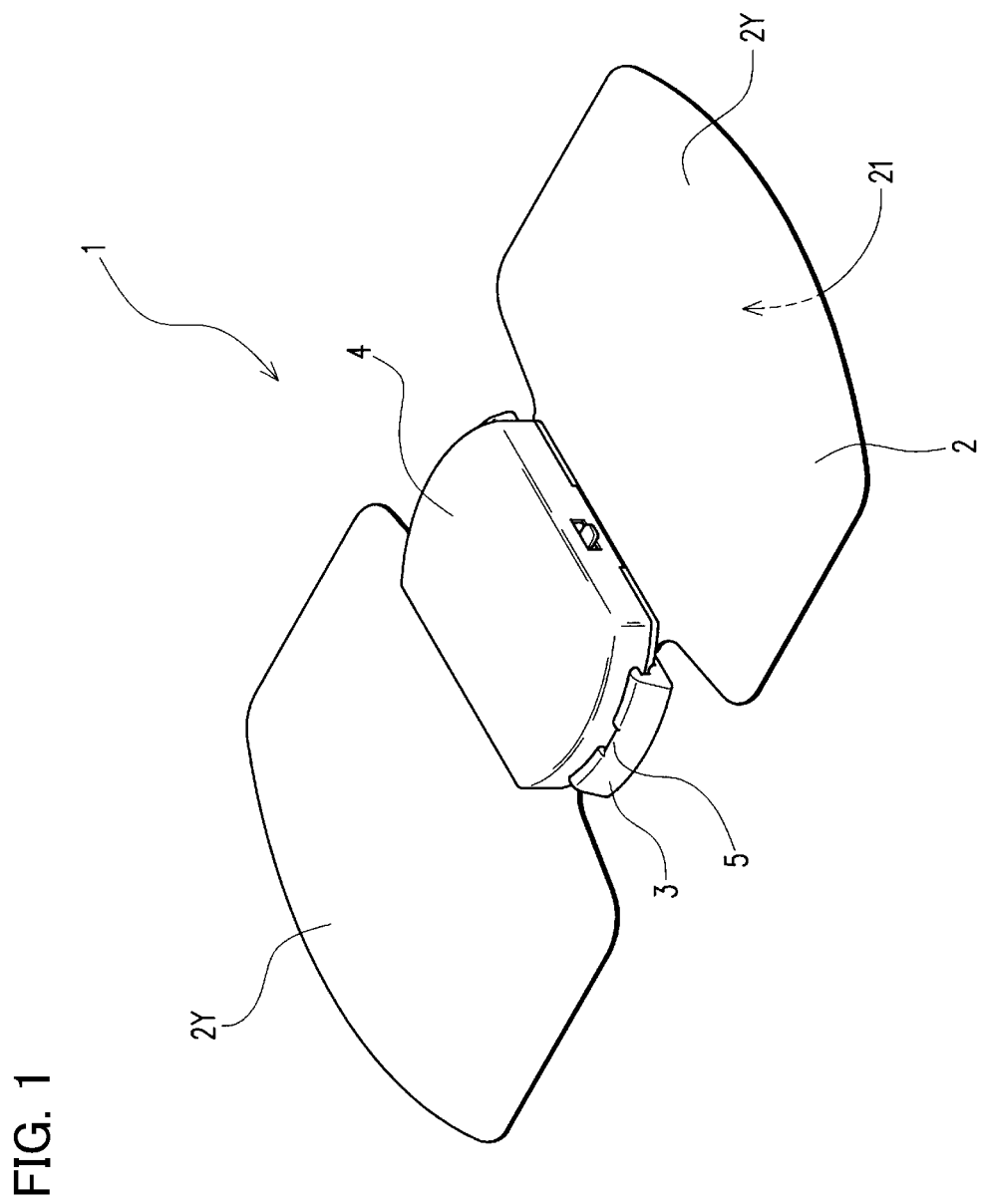
FIG. 1 is a perspective view showing a low-frequency treatment device according to an embodiment of the present invention.

Next, the present invention will be described by means of an embodiment. Note that the vertical direction in the following description is the vertical direction of a low-frequency treatment device 1 in the state shown in FIG. 1. The low-frequency treatment device 1 of the present embodiment is a cordless type. The low-frequency treatment device 1 includes a pad 2, a holder 3, and a main body portion 4, which are integrated during use, and these portions can be combined to perform treatment.

The pad 2 is a sheet-like portion that is to be attached to the body of a user. The pad 2 includes conductive layers 2a that supply a low-frequency pulse current to the user. The conductive layers 2a are exposed on the surface (lower surface) of a body-side portion 21 facing the body side of the pad 2. The pad 2 is attached to the body of the user by adhering the body-side portion 21 to the skin of the user via conductive gel (not shown).

The pad 2 includes carbon layers, which are conductors, and are layered through printing on the surface of a base material (not shown) made of a flexible synthetic resin, and the carbon layers are the conducting layers 2a. The conductive layers 2a are provided according to their polarities (positive pole, negative pole) when current is applied. Note that since current is sometimes applied to the pad 2 with the polarities switched alternatingly, the polarities are variable instead of a positive pole-dedicated conductive layer 2a and a negative pole-dedicated conductive layer 2a existing in a fixed manner.

Figure 2:
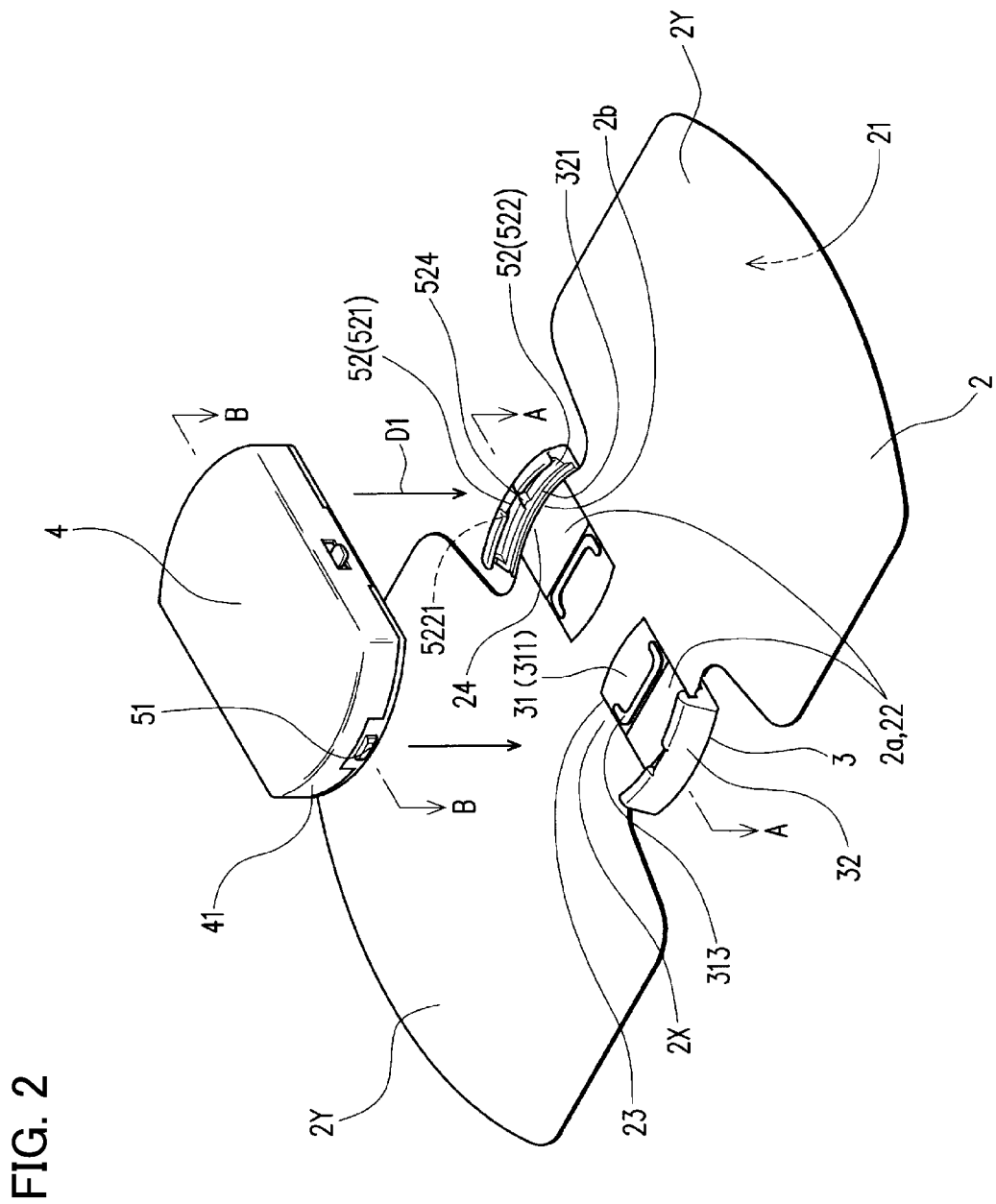
FIG. 2 is an exploded perspective view showing a state in which a holder and a pad of the low-frequency treatment device are separated from a main body portion.

As shown in FIG. 2, the pad 2 includes an attachment portion 2X that is attached to an approximately rectangular (specifically, an approximately rectangular shape with both ends in the length direction rounded) holder 3, and treatment portions 2Y that extend in at least one direction from the attachment portion 2X and at which the conductive layers 2a are exposed. The treatment portions 2Y of the present embodiment extend in mutually opposite directions from the attachment portion 2X according to their polarities. Also, the conductive layers 2a are exposed over the entire surface of the body-side portion 21, which is the bottom surface of the treatment portions 2Y.

The attachment portion 2X has a squeezed shape compared to the treatment portions 2Y. In other words, the width dimension of the attachment portion 2X is formed so as to be smaller than the width dimension of the treatment portions 2Y Accordingly, the holder 3 and the main body portion 4 can be made compact. Also, the conductive layers 2a are exposed on the surface that faces the main body portion 4 of the attachment portion 2X of the pad 2, and the exposed portions are pad-side electrode portions 22. The pad-side electrode portions 22 are formed for electrical connection with main body portion-side electrode portions 43. In the present embodiment, a conductive layer 2a corresponding to one pole (e.g., the positive pole) is exposed at one end in the width direction of the attachment portion 2X, and the conductive layer 2a corresponding to the other pole (e.g., the negative pole) is exposed at the other end. Accordingly, the conductive layers 2a of the pad-side electrode portions 22 are exposed at the outer circumferential portions of the pad 2. For example, the conductive layers 2a of the pad-side electrode portions 22 can be exposed by peeling off at least a portion of a layer of the pad 2 covering the conductive layers 2a, by folding over at least a portion of the pad 2 at which the conductive layer is provided on the underside surface in the top-underside direction and thereby setting the portion exposed on the top side as the conductive layer 2a, or by overlaying a member on which a conductive layer is formed on the pad 2 in the thickness direction and using the conductive portions as the conductive layers 2a.

The holder 3 is a portion that holds the pad 2. In the present embodiment, the holder 3 is made of hard resin and holds the attachment portion 2X of the pad 2 using double-sided adhesive tape. The holder 3 includes a pad holding portion 31 that holds the attachment portion 2X of the pad 2, and a wall portion 32 that is located on both ends of the pad holding portion 31. Note that the holding of the pad 2 is not limited to being achieved using double-sided adhesive tape and can be achieved using paste or an adhesive agent, for example.

The holder 3 is a non-conductor since it is made of hard resin. For this reason, if the pad 2 is arranged over the spine on the back of the user, the holder 3, which is a non-conductor, can be aligned with the spine, and the treatment portions 2Y of the pad 2 can be arranged so as to not overlap with the spine. Accordingly, it is possible to suppress a case in which a low-frequency pulse current flows in the spine and the spinal cord of the user. Accordingly, it is possible to suppress a case in which the spine and the spinal cord are injured by the current, and therefore the low-frequency treatment device 1 can be used safely. Also, since the portion of the attachment portion 2X of the pad 2 that overlaps with the spine does not need to be covered with a separate insulating member, the configuration of the combination of the pad 2 and the holder 3 can be simplified.

Figure 3A:
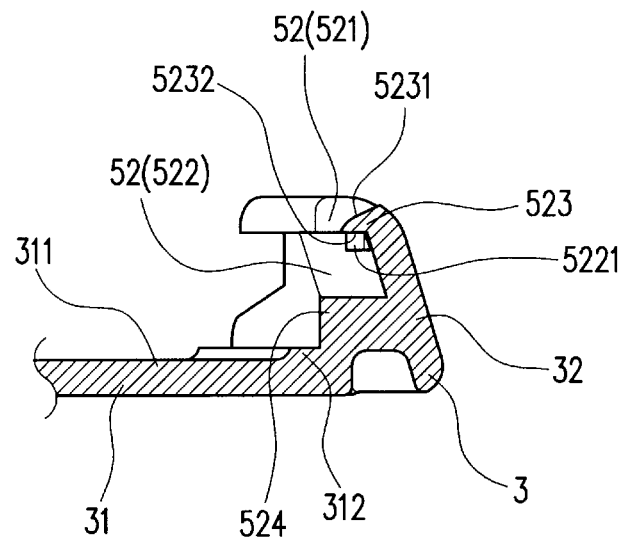
FIG. 3A is a vertical cross-sectional view showing principal portions of a vertical groove portion and a horizontal groove portion of a holder in the low-frequency treatment device, at a portion (not showing the pad) viewed in the direction of arrow A-A in FIG. 2.
Figure 5:
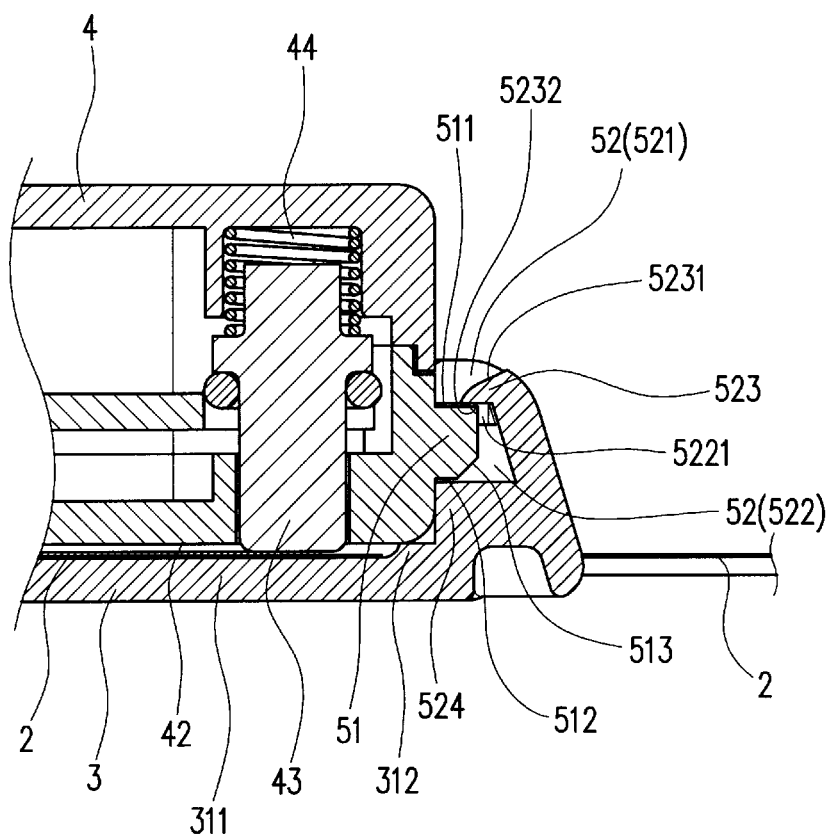
FIG. 5 is a vertical cross-sectional view showing principal portions of the holder and the pad of the low-frequency treatment device in an engaged state.

As shown in FIG. 3A, the pad holding portion 31 includes a pad contact portion 311 located toward the center, and a circumferential edge portion 312 located toward the wall portion 32. As shown in the drawings, the upper surface of the circumferential edge portion 312 is located above the upper surface of the pad contact portion 311. For this reason, in the state in which the main body portion 4 is attached to the holder 3 as shown in FIG. 5, the lower surface 42 of the main body portion 4 comes into contact with the circumferential edge portion 312.

As shown in FIG. 2, the pad 2 is overlaid on the pad contact portion 311 such that it comes into contact with the upper surface of the pad contact portion 311. Positioning protrusions 313 that are approximately U-shaped protrude upward from the pad contact portion 311, and the pad 2 can be positioned with respect to the holder 3 by aligning the edge portion of a window portion 23 that penetrates through the pad 2 in the top-underside direction with the positioning protrusions 313.

As described above, the upper surface of the circumferential edge portion 312 is located above the upper surface of the pad contact portion 311. For this reason, in the state in which the main body 4 is attached to the holder 3, the bottom surface 42 of the main body portion 4 comes into contact with the circumferential edge portion 312, and therefore as shown in FIG. 5, the upper surface of the pad 2 on the pad contact portion 311 and the bottom surface 42 of the main body portion 4 do not come into close contact, and a gap can be provided. For this reason, it is possible to suppress a case in which the main body portion 4 is contaminated by peeled-off carbon due to the bottom surface 42 rubbing against the carbon layer of the pad-side electrode portion 22. Accordingly, the low-frequency treatment device 1 can be used cleanly for a long time.

Since the pad 2 is a consumable product, it can be detached from the main body 4 at a time of replacement or the like. In the present embodiment, due to the holder 3 holding the pad 2, the holder 3 and the pad 2 are integrated, and the main body portion 4 is attached to and detached from the holder 3. The replacement of the pad 2 is performed together with the holder 3.

Figure 3B:
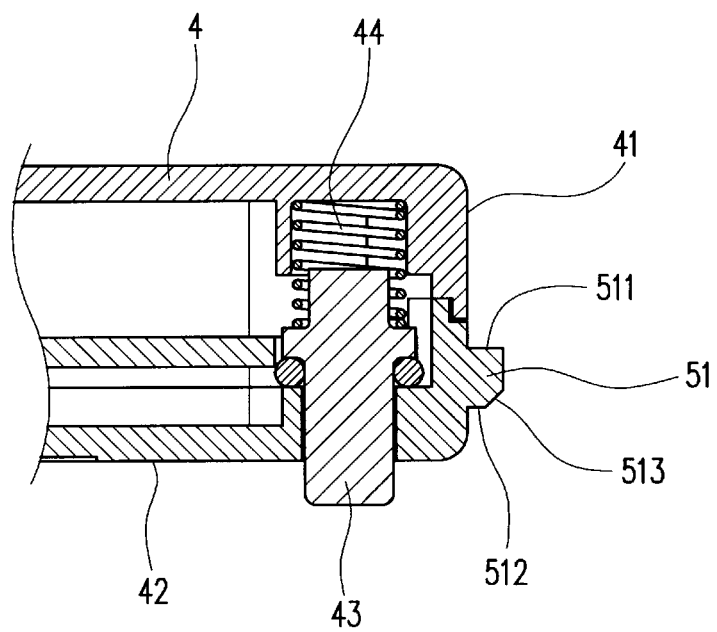
FIG. 3B is a vertical cross-sectional view showing principal portions of a main body portion-side protrusion of a main body portion (not showing the internal structure) in the low-frequency treatment device at a portion viewed in the direction of arrow B-B in FIG. 2.

The main body portion 4 is a portion that supplies a low-frequency pulse current to the conductive layers 2a of the pad 2 due to being attached to the holder 3. Inside of the main body portion 4, a power source unit such as a battery and an electrical circuit (substrate) for forming a desired low-frequency pulse current are arranged, and switches and a display unit are provided outside of the main body portion 4 (only portions thereof are illustrated in the drawings). As shown in FIG. 3B, the main body portion-side electrode portion 43 protrudes from the lower surface 42, which is a surface that faces the holder 3 of the main body portion 4, in a state of being biased by the spring 44 (the position of the main body portion-side electrode portion 43 is indicated by a two-dot chain line in FIGS. 6A and 6B as well). A main body portion-side electrode portion 43 is provided for each polarity.

In the holder 3 and the main body portion 4, a guiding engagement portion 5 is formed which is configured such that the holder 3 and the main body portion 4 engage when the main body portion 4 is attached to the holder 3 in an overlapping manner and the holder 3 and the main body portion 4 disengage when the main body portion 4 is removed from the holder 3. The guiding engagement portion 5 engages both the holder 3 and the main body portion 4 and restricts the movement direction of the main body portion 4 with respect to the holder 3 during attachment and removal of the two. Specifically, the guiding engagement portion 5 is formed such that the holder 3 and the main body portion 4 move in the direction (downward direction) D1 of approaching each other, which is the direction indicated by the arrow in FIG. 2, to achieve engagement at the time of attaching the holder 3 and the main body portion 4. Also, the guiding engagement portion 5 is formed such that the holder 3 and the main body portion 4 are disengaged due to the main body portion 4 moving with respect to the holder 3 in a direction (horizontal direction) D2 (see FIG. 6A) that intersects the direction D1 of approaching each other at the time of removing the holder 3 and the main body portion 4. Note that during the removal, movement in the direction (upward direction) opposite to the direction of movement at the time of attachment is restricted (in the present embodiment, such movement is made impossible). Also, in the present embodiment, the holder 3 and the main body portion 4 are disengaged also in the case where the main body portion 4 is moved in a clockwise direction, which is a direction opposite to the direction D2, which is a counterclockwise direction in a plan view. In this manner, the guiding engagement portion 5 can be configured such that the holder 3 and the main body portion 4 can be disengaged by moving the main body portion 4 in both horizontal directions, and the guiding engagement portion 5 can also be configured such that the holder 3 and the main body portion 4 can be disengaged by moving the main body portion 4 in only one horizontal direction.

Due to the guiding engagement portion 5 restricting the movement direction of the main body portion 4 with respect to the holder 3 in this manner, the holder 3 can be attached to the main body portion 4 with one touch (by merely pressing the main body portion 4 into the holder 3). On the other hand, regarding the removal, since the holder 3 and the main body portion 4 are disengaged by moving in the direction (horizontal direction) D2, which intersects the direction D1 of approaching each other, the holder 3 and the main body portion 4 are difficult to disengage using an external force other than a user operation. For this reason, even if the user moves during use, it is possible to suppress a case in which the main body portion 4 accidentally comes off of the holder 3. In the present embodiment in particular, due to a later-described stopper protrusion 5221, the holder 3 and the main body portion 4 are even less likely to be disengaged.

Figure 6A:
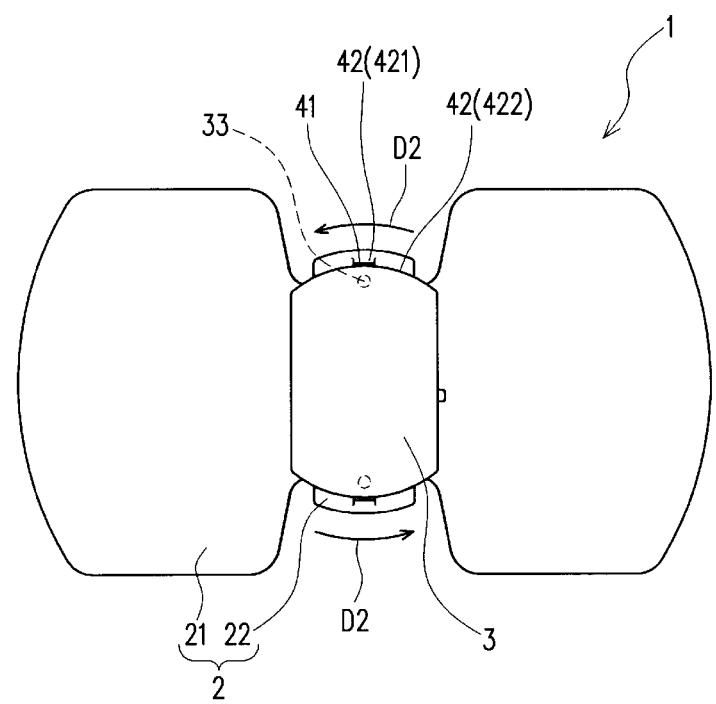
FIG. 6A is a plan view showing a state in which a main body portion is attached to the holder of the low-frequency treatment device.

The guiding engagement portion 5 is formed such that when the main body portion 4 is removed from the holder 3, the holder 3 and the main body portion 4 are disengaged due to the main body portion 4 being rotated with respect to the holder 3 in the horizontal direction D2 indicated by the arrow in FIG. 6A, for example. According to this configuration, when the holder 3 and the main body portion 4 are removed from each other, they are disengaged by being rotated about an axis oriented in the direction D1 of approaching each other, and therefore in comparison to the disengagement by means of simple parallel movement, it is possible to effectively suppress a case in which the main body portion 4 is accidentally removed from the holder 3 when the user moves during use.

Hereinafter, the guiding engagement portion 5 will be described specifically. As shown in FIG. 2, the guiding engagement portion 5 of the present embodiment includes main body portion-side protrusions 51, which are protrusions formed on the main body portion 4, and groove portions 52 that are formed on the holder 3 and into which the main body portion-side protrusions 51 fit. In this configuration, the guiding engagement portion 5 can be constituted by fitting together recesses and protrusions, and therefore the configuration can be simplified.

A pair of wall portions 32 of the holder 3 are at both ends in the lengthwise direction of the pad holding portion 31, and are located on both sides (both end sides in the width direction of the pad 2) that sandwich the main body portion 4 in a direction intersecting the direction D1 of approaching each other. The inner sides of the pair of wall portions 32 have curved shapes so as to allow rotation of the main body portion 4 in the horizontal direction D2 during removal. Vertical groove portions 521 and horizontal groove portions 522 are formed as the groove portions 52 on the inner surfaces of the wall portions 32. The vertical groove portion 521 is formed in the vertical direction, which is the direction D1 in which the holder 3 and the main body portion 4 approach each other, and the upper portion of the vertical groove portion 521 is open. The horizontal groove portion 522 is formed in the horizontal direction that intersects the vertical direction, and at least one end portion in the horizontal direction is open. In the present embodiment, the vertical groove portion 521 and the horizontal groove portion 522 are orthogonal to each other. Also, both ends in the horizontal direction of the horizontal groove portion 522 of the present embodiment are open.

The vertical cross-sectional shape of the portion at which the vertical groove portion 521 and the horizontal groove portion 522 intersect is the shape shown in FIG. 3A. A flange portion 523 that extends inward (toward the center of the pad holding portion 31) is located above the vertical groove portion 521. An introduction inclined surface 5231 is formed above the flange portion 523. The introduction inclined surface 5231 is an inclined surface that curves gradually such that it directs downward as it heads inward. A horizontal plane 5232 is formed on the lower portion of the flange portion 523. The vertical dimension of the horizontal groove portion 522 is formed slightly larger than the vertical dimension of the main body portion-side protrusion 51 formed on the main body portion 4. Accordingly, the main body portion-side protrusion 51 can move in the lengthwise direction of the horizontal groove portion 522. Also, an engagement protrusion 524 that protrudes upward from the bottom surface of the horizontal groove portion 522 is formed at the portion at which the vertical groove portion 521 and the horizontal groove portion 522 intersect.

Figure 4:
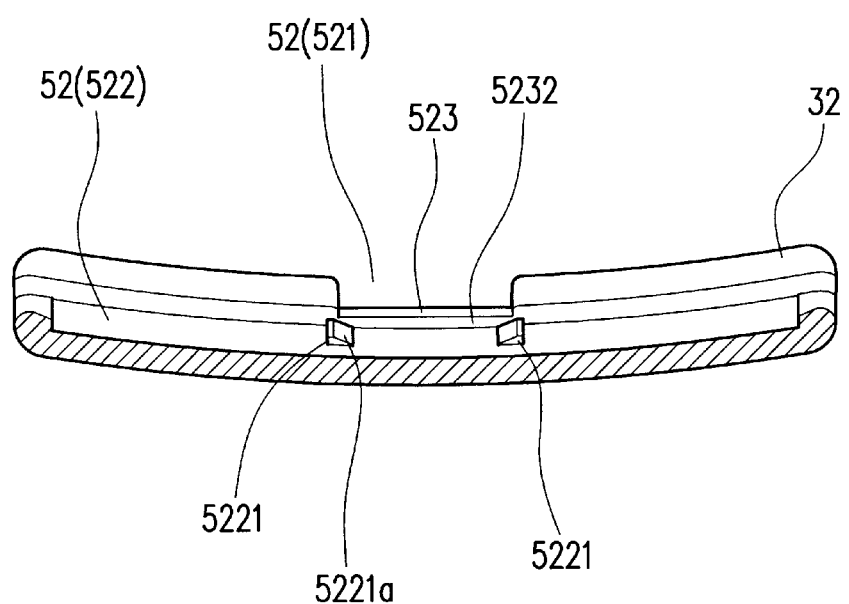
FIG. 4 is a horizontal cross-sectional perspective view showing a vertical groove portion and a horizontal groove portion of the holder of the low-frequency treatment device.

Also, as shown in FIG. 4, the horizontal groove portion 522 is provided with a pair of stopper protrusions 5221 and 5221 serving as restricting portions that restrict rotation of the main body portion 4 in the horizontal direction D2, for example, with respect to the holder 3 from the state in which the main body portion 4 is attached so as to overlap with the holder 3. This pair of stopper protrusions 5221 and 5221 are located on both sides in the horizontal direction of sandwiching the main body portion-side protrusion 51 in the attached state. When an attempt is made to move the main body portion-side protrusion 51, the main body portion-side protrusion 51 abuts against the stopper protrusions 5221. Due to this abutting, movement in the direction of disengagement of the main body portion 4 is restricted. In the present embodiment, since the holder 3 and the main body portion 4 can disengaged by moving the main body portion 4 in both horizontal directions, the stopper protrusions 5221 are formed at two locations. However, if the guiding engagement portion 5 is configured such that the holder 3 and the main body portion 4 can be disengaged by moving the main body portion 4 in only one horizontal direction, it is sufficient that a stopper protrusion 5221 is formed at only one location.

Figure 6B:
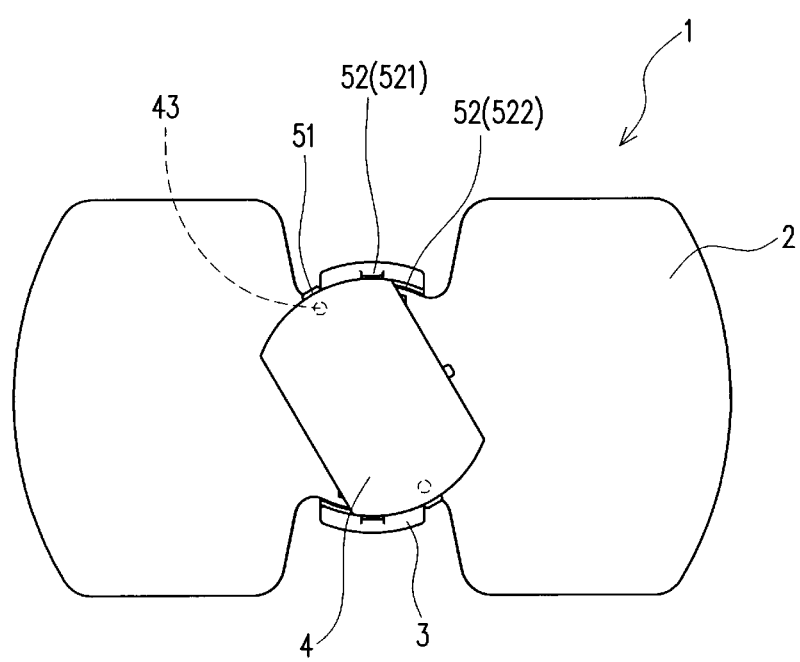
FIG. 6B is a plan view showing a state during which the rain body portion is removed from the holder of the low-frequency treatment device.

Also, when the main body portion 4 is rotated with a force exceeding a certain force, the main body portion-side protrusion 51 goes past the stopper protrusion 5221. Upon doing so, the restriction on the movement is canceled, and it becomes possible to rotate the main body portion 4 in the horizontal direction D2 shown in FIG. 6A, and as a result, as shown in FIG. 6B, the main body portion 4 can be disengaged.

As shown in En 4, an inclined surface 5221a is formed on the inner side (side facing the main body portion-side protrusion 51) of the stopper protrusion 5221. For this reason, the main body portion-side protrusion 51 comes into contact with the inclined surface 5221a and its movement is restricted. Accordingly, the holder 3 and the main body portion 4 can be disengaged by making the stopper protrusion 5221 go past the main body portion-side protrusion 51 without requiring excessive force.

According to the above description, due to the pair of stopper protrusions 5221 and 5221 being formed in the horizontal groove portion 522, it is possible to suppress a case in which the main body portion 4 rotates in the horizontal direction D2 due to the stopper protrusions 5221. For this reason, the engaged state can be reliably maintained. Also, since a clicking sound and sensation (a click feeling) are conveyed to the user at the time of going past, the user can understand that the main body portion 4 is no longer in the engaged state. Accordingly, since the click feeling is conveyed to the user even if the main body portion 4 is rotated in error, the user can be prompted to re-attach the main body portion 4 if the rotation is in error.

On the other hand, the main body portion-side protrusions 51 that can move along the vertical groove portions 521 of the holder 3 and can move along the horizontal groove portions 522 are formed on the side surfaces 41 of the main body portion 4 that face the wall portions 32 of the holder 3. According to this configuration, at the time of attachment, the vertical groove portions 521 and the horizontal groove portions 522 are provided in the holder 3, which is a side that basically does not move, and the main body portion-side protrusions 51 are formed on the main body portion 4, which is a side that is moved. Accordingly, positioning of the two is easy.

The vertical cross-sectional shape of the main body portion-side protrusion 51 is shown in FIG. 3B. A horizontal surface 511 is formed on the upper portion of the main body portion-side protrusion 51, and a horizontal surface 512 and tapered surface 513 are formed on the lower portion. The horizontal surface 512 on the lower portion comes into contact with the engagement protrusion 524 when the main body portion 4 is attached to the holder 3. Also, the tapered surface 513 is a flat inclined surface at which the protrusion amount of the main body portion-side protrusion 51 contracts as it heads downward.

Note that as shown in FIG. 2, the main body portion-side protrusion 51 is located below the center in the vertical direction of the side surface 41. For this reason, the main body portion-side protrusion 51 is at a position that is asymmetrical in the vertical direction. For this reason, even if the user attempts to attach the main body portion 4 to the holder 3 upside-down, the attachment cannot be performed since the position of the main body portion-side protrusion 51 (position in the vertical direction) is not aligned with the vertical groove portion 521 on the holder 3 side. For this reason, erroneous attachment can be suppressed.

When the main body portion 4 is attached to the holder 3, the tapered surfaces 513 of the main body portion-side protrusions 51 come into contact with the flange portions 523 of the vertical groove portions 521. When the main body portion-side protrusions 51 are aligned with the flange portions 523 and the main body portion 4 is pressed from above, the flange portions 523 pressed by the main body portion-side protrusions 51 deform elastically since the holder 3 is made of resin, and the main body portion-side protrusions 51 move below the flange portions 523, or in other words, inside of the vertical groove portions 522. As a result, the horizontal surfaces 512 on the lower portions of the main body portion-side protrusions 51 come into contact with the engagement protrusions 524. In this state, the main body portion-side protrusions 51 are interposed between the horizontal surfaces 5232 of the flange portions 523 and the engagement protrusions 524 and enter the engaged state shown in FIG. 5. Note that when the main body portion-side protrusions 51 move, the elastic deformation of the flange portion 523 is restored. At this time, the clicking sound and sensation (click feeling) are conveyed to the user, and therefore the user can recognize that the attachment was performed correctly.

Note that as shown in FIG. 3A and FIG. 5, the flange portion 523 is formed such that the vertical dimension becomes smaller (rigidity decreases) as it heads inward. For this reason, the main body portion-side protrusion. 51 can be moved inside of the horizontal groove portion 522 even if the main body portion 4 is not pressed down with a large force.

In the engaged state shown in FIG. 5, even if an attempt is made to move the main body portion-side protrusion 51 upward, the movement cannot be performed since the horizontal surface 5232 of the flange portion 523 and the horizontal surface 511 of the main body portion-side protrusion 51 come into contact. Accordingly, the main body portion 4 can be reliably engaged with the holder 3.

Also, in order to cancel the engaged state, the main body portion 4 is rotated counterclockwise as shown in FIG. 6A, for example, whereby the main body portion-side protrusions 51 are removed from the engagement protrusions 524, are moved in the lengthwise direction of the vertical groove portions 522, and can escape from the vertical groove portions 522 as shown in FIG. 6B. Note that in the present embodiment, the main body portion-side protrusions 51 can escape from the horizontal groove portions 522 also in the case of being rotated clockwise, which is the direction opposite to that stated above. When the main body portion-side protrusions 51 are removed from the engagement protrusions 524, since the engagement protrusions 524 are no longer present, an allowance can be produced in the vertical direction dimension based on the main body portion-side protrusions 51 in the horizontal groove portions 522, and therefore the main body portion 4 can be rotated easily. Since the engaged state is canceled in the state shown in FIG. 6B, the main body portion 4 can be removed from the holder 3 by moving the main body portion 4 upward.

Here, the main body portion-side electrode portions 43 are provided at positions different from those of the main body portion-side protrusions 51, as indicated by the broken lines in FIGS. 6A and 6B. On the other hand, at the attachment portion 2X, as shown in FIG. 2, the pad 2 is held on the holder 3 such that the outer circumferential edges 2b approximately conform to the inner edges 321 of the wall portions 32 in the holder 3. When the main body portion 4 is attached to the holder 3, the main body portion-side electrode portions 43 supply a low-frequency pulse current due to coming into contact with the pad-side electrode portions 22 of the pad 2 located on the holder 3.

In this manner, when the main body portion-side electrode portions 43 are in contact with the pad-side electrode portions 22, the holder 3 and the main body portion 4 can be engaged by the guiding engagement portion 5. For this reason, the contact between the electrode portions can be made strong. Accordingly, the state of electrical conduction between the pad 2 and the main body portion 4 can made stable.

Also, the guiding engagement portion 5 is in charge of the physical connection between the holder 3 and the main body portion 4, and the main body portion-side electrode portions 43 are in charge of the electrical connection between the pad 2 and the main body portion 4. For this reason, it is possible to supply current more stably compared to a configuration in which both connections are combined, such as a configuration in which fitting and electrical conduction are achieved using a snap member that is made of metal and achieves fitting of a recess and a protrusion, for example. Furthermore, as long as the engaged state of the guiding engagement portion 5 is maintained due to the guiding engagement portion 5 and the main body portion-side electrode portions 43 being near each other, the contact state between the main body portion-side electrode portions 43 and the pad-side electrode portions 22 is not likely to be impaired, and the low-frequency pulse current can be reliably supplied.

Also, at the attachment portion 2X, a curved portion 24 that approximately matches the curve of the wall portion 32 of the holder 3 is included on the outer circumferential edge 2b of the pad 2. In this manner, since the pad 2 has the curved outer edges conforming to the direction of rotation at the time of removal, it is possible to suppress a circumstance in which the pad 2 gets caught on the guiding engagement portion 5, such as the main body portion-side protrusions 51, and comes off during removal, and for this reason, the low-frequency treatment device 1 can be used comfortably.

Although an embodiment of the present invention has been described above, the present invention is not limited to the above-described embodiment, and various modifications can be added thereto without departing from the gist of the present invention.

For example, pads 2 may be formed separately for each polarity. Also, in the above-described embodiment, the exposed portions of the conductive layers 2a that are formed for the electrical connection with the main body portion-side electrode portions 43 are located on both sides in the width direction of the attachment portion 2X, but there is no limitation to this, and another position such as the center in the width direction may be used, as long as it overlaps with the main body portion 4 when attached. Also, conversely to the above-described embodiment, protrusions may be formed on the holder 3 and groove portions may be formed on the main body portion 4.

Also, the guiding engagement portion 5 of the above-described embodiment is formed spanning between the wall portions 32 (groove portions 52) located on both ends in the lengthwise direction of the pad holding portion 31 of the holder 3 and the side surfaces 41 (main body portion-side protrusions 51) that face the wall portions 32 of the holder 3 in the main body portion 4. However, the guiding engagement portion 5 is not limited to this, and may be formed at another position.

Figure 7:
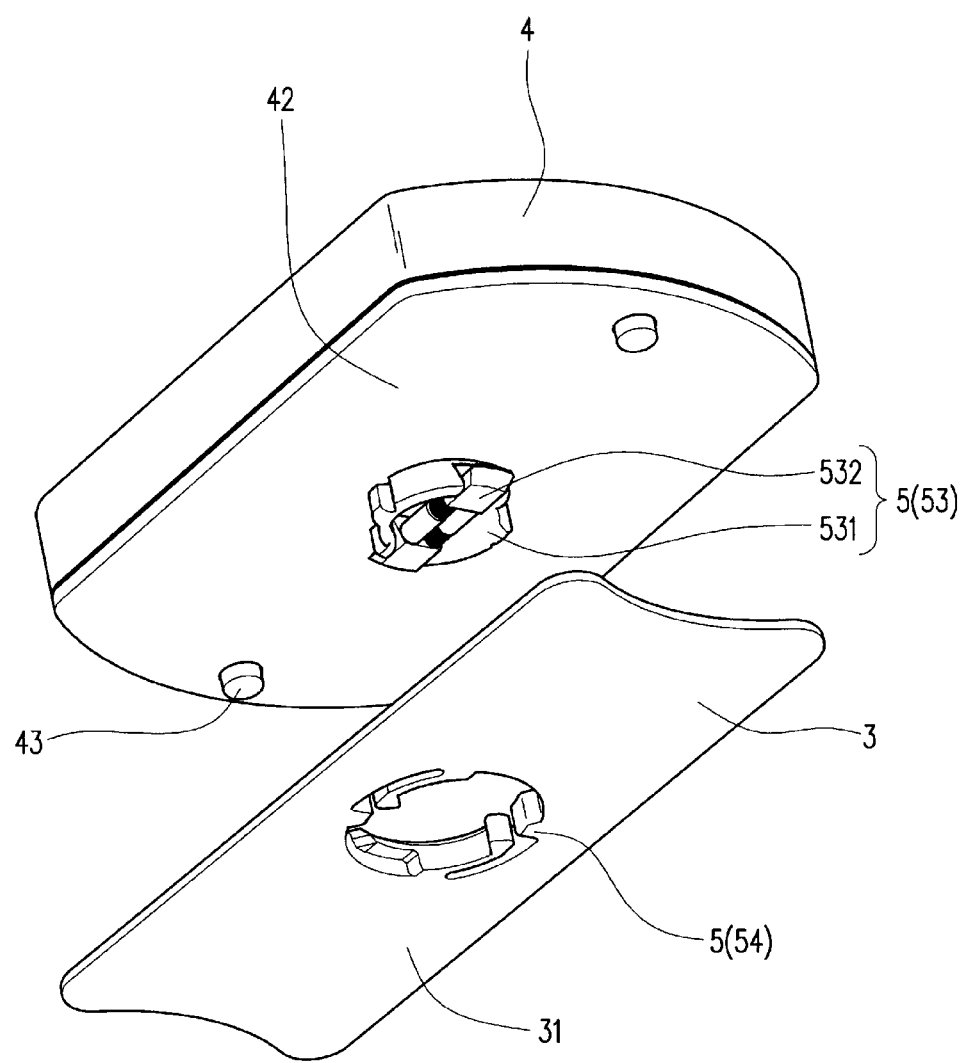
FIG. 7 is a perspective view taken from a bottom surface side, showing an overall structure of the holder (not including the pad) and the main body portion in the low-frequency treatment device according to another embodiment of the present invention.

For example, as shown in FIG. 7, the guiding engagement portion 5 can also be formed spanning across the center in the lengthwise direction of the pad holding portion 31 of the holder 3 and the center in the lengthwise direction of the main body portion 4. The guiding engagement portion 5 shown in FIG. 7 includes a main body portion-side protrusion 53 composed of a protrusion main body 531 formed at the center of the lower surface 42 of the main body portion 4 and claw portions that can extend and retract with respect to the protrusion main body 531, and a recessed portion 54 that is formed at the center of the holder 3 and into which the main body portion-side protrusion 53 fits.

Similarly to the above-described embodiment, the guiding engagement portion 5 engages both the holder 3 and the main body portion 4 and restricts the movement direction of the main body portion 4 with respect to the holder 3 during attachment and removal of the two. In other words, with this guiding engagement portion 5 as well, engagement is achieved by moving the two in the direction (downward direction) of approaching each other during attachment of the two. Also, the guiding engagement portion 5 is formed such that during removal of the two, the two are disengaged due to the main body portion 4 moving with respect to the holder 3 in a direction (horizontal direction) that intersects the direction of approaching each other. Also, during removal, movement in the direction (upward direction) opposite to the movement direction during the attachment is restricted.

Note that the guiding engagement portion 5 shown in FIG. 7 only schematically indicates an example of a mode other than the above-described embodiment. The guiding engagement portion 5 can be implemented in various other modes.

REFERENCE SIGNS LIST

1. Low-frequency treatment device
2. Pad
2X Attachment portion
2Y Treatment portion
2a Conductive layer
2b Outer circumferential edge of pad
22 Pad-side electrode portion
24 Curved portion
3 Holder
32 Wall portion
321 Inner edge of wall portion
4 Main body portion
41 Side surface
43 Main body portion-side electrode portion
5 Guiding engagement portion
51 Protrusion, main body portion-side protrusion
52 Groove portion
521 Vertical groove portion
522 Horizontal groove portion
5221 Restricting portion, stopper protrusion
D1 Direction of approaching each other
D2 Direction intersecting direction of approaching each other, horizontal direction

The invention claimed is:

1. A low-frequency treatment device comprising:
a pad that is to be attached to a body of a user and is configured to supply a low-frequency pulse current to the user;
a holder configured to hold the pad;
a main body portion configured to supply a low-frequency pulse current to the pad by being attached to the holder; and a guiding engagement portion configured such that the holder and the main body portion engage in a state in which the main body portion is attached to the holder, and the holder and the main body portion are disengaged in a state in which the main body portion is removed from the holder, wherein:
the guiding engagement portion is formed so as to
allow the holder and the main body portion to engage by moving in a direction of approaching each other during the attachment, and
during the removal, disengage the holder and the main body portion by restricting movement in a direction opposite to the movement direction during the attachment and allowing the main body portion to move with respect to the holder in a direction intersecting the direction of approaching each other,
the guiding engagement portion includes a protrusion formed on one of the holder and the main body portion, and a groove portion formed on the other and in which the protrusion fits,
the holder includes a set of wall portions that are located on both sides of the main body portion in the direction intersecting the direction of approaching each other, inner sides of the wall portions having a curved shape so as to allow rotation of the main body portion,
on the inner surfaces of the wall portions, vertical groove portions that are formed in a vertical direction, which is the direction of approaching each other, and open upward, and a set of horizontal groove portions that are formed in the direction intersecting the vertical direction and are open at at least one end portion in a horizontal direction are formed as the groove portions, and
a set of main body portion-side protrusions that can move along the vertical groove portions and the horizontal groove portions are formed on side surfaces of the main body portion that face the wall portions.

2. The low-frequency treatment device according to claim 1, wherein the guiding engagement portion is formed such that during the removal, the holder and the main body portion are disengaged due to the main body portion being rotated with respect to the holder about an axis oriented in the direction of approaching each other.

3. The low-frequency treatment device according to claim 1, wherein at least one of the set of horizontal groove portions is provided with a restricting portion that restricts rotation of the main body portion with respect to the holder in the direction intersecting the direction of approaching each other, from a state in which the main body portion is attached to the holder.

4. The low-frequency treatment device according to claim 1, wherein:
the main body portion includes a main body portion-side electrode portion configured to supply a low-frequency pulse current to the pad, the main body portion-side electrode portion protruding from a surface facing the holder,
the pad includes an attachment portion to be attached to the holder,
the attachment portion includes a pad-side electrode portion on a surface facing the main body portion, and
the main body portion-side electrode portion comes into contact with the pad-side electrode portion when the main body portion is attached to the holder, and thus a low-frequency pulse current is supplied from the main body portion to the pad.

5. The low-frequency treatment device according to claim 1, wherein the holder is composed of a non-conductor.

6. A pad for a low-frequency treatment device, which is to be used in the low-frequency treatment device according to claim 1, the pad comprising
an attachment portion to be attached to the holder of the low-frequency treatment device, and a treatment portion that extends in at least one direction from the attachment portion and at which a conductive layer composed of a conductor is exposed, wherein:
a width dimension of the attachment portion is formed to be smaller than a width dimension of the treatment portion, and
an outer circumferential edge of the attachment portion includes curve portions that approximately match the curves of the wall portions of the low-frequency treatment device.

7. A main body portion for a low-frequency treatment device that is configured to supply a low-frequency pulse current to a pad configured to be attached to a body of a user and supply the low-frequency pulse current to the user, by being attached to a holder for holding the pad, the main body comprising
a guiding engagement portion configured such that the holder and the main body portion engage in a state in which the main body portion is attached to the holder, and the holder and the main body portion are disengaged in a state in which the main body portion is removed from the holder, wherein:
the guiding engagement portion is formed so as to
allow the holder and the main body portion to engage by moving in a direction of approaching each other during the attachment, and
during the removal, disengage the holder and the main body portion by restricting movement in a direction opposite to the movement direction during the attachment and allowing the main body portion to move with respect to the holder in a direction intersecting the direction of approaching each other,
the guiding engagement portion includes a protrusion formed on one of the holder and the main body portion, and a groove portion formed on the other and in which the protrusion fits,
the holder includes a set of wall portions that are located on both sides of the main body portion in the direction intersecting the direction of approaching each other, inner sides of the wall portions having a curved shape so as to allow rotation of the main body portion,
on the inner surfaces of the wall portions, vertical groove portions that are formed in a vertical direction, which is the direction of approaching each other, and open upward, and a set of horizontal groove portions that are formed in the direction intersecting the vertical direction and are open at at least one end portion in a horizontal direction are formed as the groove portions, and
a set of main body portion-side protrusions that can move along the vertical groove portions and the horizontal groove portions are formed on side surfaces of the main body portion that face the wall portions.

8. A holder for a low-frequency treatment device configured to hold a pad that is to be attached to a body of a user and supply a low-frequency pulse current to the user, the holder being attached to a main body portion configured to supply the low-frequency pulse current to the pad, the holder comprising a guiding engagement portion configured such that the holder and the main body portion engage in a state in which the main body portion is attached, and the holder and the main body portion are disengaged in a state in which the main body portion is removed, wherein:

the guiding engagement portion is formed so as to
- allow the holder and the main body portion to engage by moving in a direction of approaching each other during the attachment, and
- during the removal, disengage the holder and the main body portion by restricting movement in a direction opposite to the movement direction during the attachment and allowing the main body portion to move with respect to the holder in a direction intersecting the direction of approaching each other, the guiding engagement portion includes a protrusion formed on one of the holder and the main body portion, and a groove portion formed on the other and in which the protrusion fits, the holder includes a set of wall portions that are located on both sides of the main body portion in the direction intersecting the direction of approaching each other, inner sides of the wall portions having a curved shape so as to allow rotation of the main body portion, on the inner surfaces of the wall portions, vertical groove portions that are formed in a vertical direction, which is the direction of approaching each other, and open upward, and a set of horizontal groove portions that are formed in the direction intersecting the vertical direction and are open at at least one end portion in a horizontal direction are formed as the groove portions, and a set of main body portion-side protrusions that can move along the vertical groove portions and the horizontal groove portions are formed on side surfaces of the main body portion that face the wall portions.

9. A combination of a pad and a holder for a low-frequency treatment device, comprising a pad that is to be attached to a body of a user and is configured to supply a low-frequency pulse current to the user, and a holder configured to hold the pad, wherein:

the holder includes a guiding engagement portion configured such that the holder and a main body portion for supplying a low-frequency pulse current to the pad engage in a state in which the main body portion is attached, and the holder and the main body portion are disengaged in a state in which the main body portion is removed, the guiding engagement portion is formed so as to
- allow the holder and the main body portion to engage by moving in a direction of approaching each other during the attachment, and
- during the removal, disengage the holder and the main body portion by restricting movement in a direction opposite to the movement direction during the attachment, and allowing the main body portion to move with respect to the holder in a direction intersecting the direction of approaching each other, the guiding engagement portion includes a protrusion formed on one of the holder and the main body portion, and a groove portion formed on the other and in which the protrusion fits, the holder includes a set of wall portions that are located on both sides of the main body portion in the direction intersecting the direction of approaching each other, inner sides of the wall portions having a curved shape so as to allow rotation of the main body portion, on the inner surfaces of the wall portions, vertical groove portions that are formed in a vertical direction, which is the direction of approaching each other, and open upward, and a set of horizontal groove portions that are formed in the direction intersecting the vertical direction and are open at at least one end portion in a horizontal direction are formed as the groove portions, and a set of main body portion-side protrusions that can move along the vertical groove portions and the horizontal groove portions are formed on side surfaces of the main body portion that face the wall portions.

10. The combination of a pad and a holder for a low-frequency treatment device according to claim 9, wherein the holder is composed of a non-conductor.

* * * * *